(12) United States Patent
Souza et al.

(10) Patent No.: US 7,795,459 B2
(45) Date of Patent: Sep. 14, 2010

(54) PARICALCITOL PURIFICATION

(75) Inventors: Fabio Eduardo Silva e Souza, Mississauga (CA); Ming Pan, Mississauga (CA); Kathleen Da Silva Turcot, Toronto (CA)

(73) Assignee: Alphora Research Inc., Mississauga (CA)

( * ) Notice: Subject to any disclaimer, the term of this patent is extended or adjusted under 35 U.S.C. 154(b) by 0 days.

(21) Appl. No.: 12/431,068

(22) Filed: Apr. 28, 2009

(65) Prior Publication Data

US 2010/0063330 A1   Mar. 11, 2010

(30) Foreign Application Priority Data

Sep. 11, 2008   (CA) .................................... 2639477

(51) Int. Cl.
*C07C 401/00* (2006.01)
*C07C 37/84* (2006.01)

(52) U.S. Cl. .................. 552/653; 568/719; 568/749

(58) Field of Classification Search .............. None
See application file for complete search history.

(56) References Cited

U.S. PATENT DOCUMENTS

| 5,086,191 | A | 2/1992 | DeLuca et al. |
| 5,281,731 | A | 1/1994 | DeLuca et al. |
| 2007/0093458 | A1 | 4/2007 | Schwartz et al. |
| 2007/0149489 | A1* | 6/2007 | Schwartz et al. ............ 514/167 |
| 2009/0275768 | A1* | 11/2009 | Ng et al. ..................... 552/653 |

FOREIGN PATENT DOCUMENTS

WO    WO2007011951    1/2007

\* cited by examiner

*Primary Examiner*—Brian J Davis
(74) *Attorney, Agent, or Firm*—Lang Michener LLP

(57) ABSTRACT

Paricalcitol, a synthetic vitamin D analog, is purified to a purity greater than 99.7% by crystallization from solution in isopropyl acetate solvent, followed by filtration and vacuum drying. Isopropyl acetate appears to be unique among commonly available and pharmaceutically acceptable solvents in its ability to precipitate paricalcitol in this high purity, essentially free of isomers thereof.

14 Claims, No Drawings

PARICALCITOL PURIFICATION

FIELD OF THE INVENTION

This invention relates to the vitamin D analog paricalcitol, and more particularly to methods for its purification.

BACKGROUND OF THE INVENTION AND PRIOR ART

Paricalcitol (1) is a synthetically manufactured vitamin D analog developed for the treatment of secondary hyperparathyroidism associated with chronic renal failure.

The known synthetic route to paricalcitol utilizes 25-hydroxyvitamin D2 (2) as the key starting material, but this compound is quite costly and has very limited commercial availability. As a result, alternative syntheses to compound 2 and its derivatives have been developed, mostly based on the functionalization of the Inhoffen-Lythgoe diol (3).

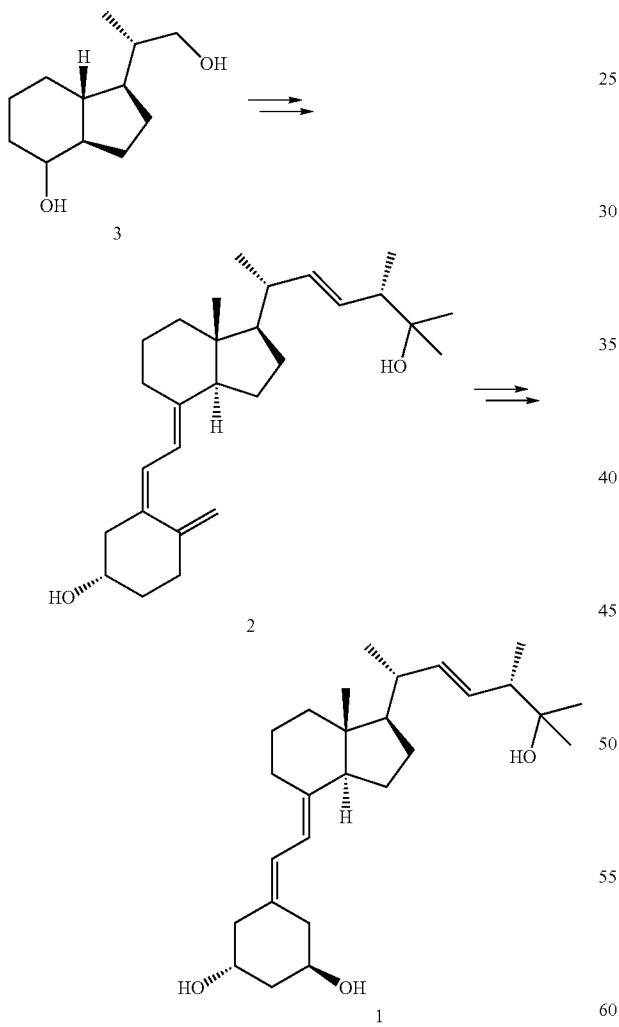

Such approaches involve a significant number of complex chemical transformations, with formation of several impurities, many of which carry through to the final active pharmaceutical ingredient (API). Of particular concern is the C20 epimer of paricalcitol, so similar in structure that even the HPLC analytical method listed in the United States Pharmacopeia fails to resolve both compounds.

U.S. Pat. Nos. 5,281,731 and 5,086,191 describe the purification of paricalcitol by preparative HPLC, but the cost and labor associated with this method make it undesirable for large scale manufacturing. More recently, published patent application US 2007/0093458 discloses crystallization procedures for the purification of paricalcitol. However, the examples given produce material of insufficient purity and/or in relatively low yields. Furthermore, the procedures described are volumetrically inefficient and many of them also require precise control of solvent ratios, volumes and temperatures.

SUMMARY OF THE INVENTION

The present invention provides a simple process for the purification of crude paricalcitol into API quality material. It comprises crystallization of solid impure paricalcitol from solution in isopropyl acetate. Recovery of paricalcitol is usually greater than 80%. Purity of the isolated material is usually greater than 99.7%, and the amount of C20 epimer is reduced by at least 60%. Particularly impure samples can be purified by successive such crystallizations.

DESCRIPTION OF THE PREFERRED EMBODIMENTS

Isopropyl acetate appears to be unique among industrially acceptable solvents in its ability to dissolve paricalcitol at temperatures close to the boiling point of the solvent and selectively precipitate paricalcitol on cooling, in this high degree of purity, to the substantially complete exclusion of other isomers. Moreover, this solvent is suitably volatile, relatively inexpensive, safe and non-toxic, with a high degree of pharmaceutical industry acceptability.

In the process, solid impure paricalcitol is preferably dissolved in isopropyl acetate at reflux temperatures, and crystallization is achieved by cooling the solution to room temperature or below. A solvent to substrate ratio of about 40:1 to 60:1, preferably about 50:1 (v/w) is suitably used. The solid impure paricalcitol is preferably obtained by trituration of crude paricalcitol with tert-butyl methyl ether followed by filtration. MTBE is a particularly desirable medium for the trituration, on account of its acceptable volatility (leaving little residue) and its industry acceptability.

SPECIFIC DESCRIPTION OF THE MOST PREFERRED EMBODIMENT

Example 1

Trituration of Crude Paricalcitol

Crude Paricalcitol (3.84 g, theoretical Paricalcitol content 3.1 µg) was triturated with MTBE (75 mL) at room temperature for 30 minutes, collected by filtration and washed with additional MTBE (20 mL). After drying under high vacuum at room temperature for 24 h, Paricalcitol was isolated as a white solid (2.67 g, 85% yield).

Example 2

Crystallization

Paricalcitol prepared as in Example 1 (5.34 g) was suspended in isopropyl acetate (240 mL) and refluxed until all solids had dissolved. The resulting solution was filtered hot, and precipitation was immediately observed. The suspension was allowed to cool down to ambient temperature over a 2 h period, after which it was cooled to 4° C. (refrigerator) for 1.5 h. The solids were collected by filtration and dried under high vacuum at room temperature for 18 h to give Paricalcitol as a crystalline white powder (4.59 g, 86% recovery), with 99.87% purity, as determined by HPLC.

What is claimed is:

1. A process for purifying paricalcitol, which comprises:
   i. dissolving a solid impure paricalcitol composition in isopropyl acetate solvent;
   ii. and recovering purified paricalcitol from the solution by crystallization.

2. The process of claim 1 wherein the dissolution in isopropyl acetate is conducted at elevated temperature, and crystallization is achieved by cooling.

3. The process of claim 2 wherein the dissolution takes place under reflux and cooling is conducted to room temperature or below.

4. The process of claim 1 wherein the solid impure paricalcitol composition is the solid product resulting from trituration of crude paricalcitol with t-butyl methyl ether.

5. The process of claim 4 wherein the trituration takes place at room temperature.

6. The process of claim 1 wherein the recovered paricalcitol is subjected to a second crystallization from isopropyl acetate.

7. The process of claim 6 wherein the purified paricalcitol is recovered by filtration and subsequently dried under high vacuum.

8. The process of claim 1 wherein the solvent to substrate ratio in the crystallization step is from about 40:1 to about 60:1 (v/w).

9. The process of claim 1 wherein the purified paricalcitol is recovered by filtration and subsequently dried under high vacuum.

10. The process of claim 3 wherein the purified paricalcitol is recovered by filtration and subsequently dried under high vacuum.

11. The process of claim 5 wherein the purified paricalcitol is recovered by filtration and subsequently dried under high vacuum.

12. The process of claim 3 wherein the solid impure paricalcitol composition is the solid product resulting from trituration of crude paricalcitol with t-butyl methyl ether.

13. The process of claim 12 wherein the trituration takes place at room temperature.

14. The process of claim 13 wherein the purified paricalcitol is recovered by filtration and subsequently dried under high vacuum.

* * * * *